US009018018B2

United States Patent
Amrein et al.

(10) Patent No.: US 9,018,018 B2
(45) Date of Patent: Apr. 28, 2015

(54) METHOD AND APPARATUS FOR DETERMINING THE CELL ACTIVATION OF A TARGET CELL BY AN ACTIVATOR

(75) Inventors: Matthias Amrein, Calgary (CA); Yan Shi, Calgary (CA)

(73) Assignee: JPK Instruments AG, Berlin (DE)

(*) Notice: Subject to any disclaimer, the term of this patent is extended or adjusted under 35 U.S.C. 154(b) by 690 days.

(21) Appl. No.: 12/486,674

(22) Filed: Jun. 17, 2009

(65) Prior Publication Data

US 2010/0035277 A1    Feb. 11, 2010

(30) Foreign Application Priority Data

Jun. 17, 2008 (DE) .................. 10 2008 028 429
Aug. 4, 2008 (DE) .................. 10 2008 036 064

(51) Int. Cl.
| | |
|---|---|
| G01N 33/00 | (2006.01) |
| G01Q 60/42 | (2010.01) |
| B82Y 35/00 | (2011.01) |
| G01N 33/50 | (2006.01) |
| G01Q 20/00 | (2010.01) |

(52) U.S. Cl.
CPC ............. G01Q 60/42 (2013.01); *G01Q 20/00* (2013.01); B82Y 35/00 (2013.01); G01N 33/5008 (2013.01)

(58) Field of Classification Search
None
See application file for complete search history.

(56) References Cited

U.S. PATENT DOCUMENTS

2005/0123563 A1* 6/2005 Doranz et al. ............. 424/204.1
2005/0239047 A1* 10/2005 Gimzewski et al. ............. 435/4
2010/0261159 A1* 10/2010 Hess et al. .................. 435/6

OTHER PUBLICATIONS

Evans et al (1991) Biophysical Journal 59: 838-848.*
Taubenberger et al (2007) Molecular Biology of the Cell 18:1634-1644.*
Park et al. (2008) Lap Chip 8:1034-1041.*
Anna Taubenberger et al., "Revealing Early Steps of α2β1 Integrin-mediated Adhesion to Collagen Type I by Using Single-Cell Force Spectroscopy", Molecular Biology of the Cell, vol. 18, 1634-1644, May 2007, The American Society for Cell Biology.

* cited by examiner

*Primary Examiner* — Bao Thuy L Nguyen
*Assistant Examiner* — Richard Moerschell
(74) *Attorney, Agent, or Firm* — Leason Ellis LLP

(57) ABSTRACT

The invention relates to a method and a device for determining the cell activation of a target cell by an activator, said method having the following steps: provision of a probe measuring device with a probe sample arrangement having a measuring probe and a sample holder; loading of the probe sample arrangement with a target cell and with an activator assigned to the target cell, the measuring probe being loaded with the activator, and the sample holder being loaded with the target cell, or vice versa; relative mutual displacement of the measuring probe and the sample holder until contact is made between the target cell and the activator by means of a displacement apparatus of the probe measuring device; recording of measurement values, indicating binding between the target cell and the activator, for the measuring probe with the probe measuring device during the relative displacement of the measuring probe and the sample holder; and determination of a dimension for the cell activation of the target cell from the measurement values recorded.

Figure 1:
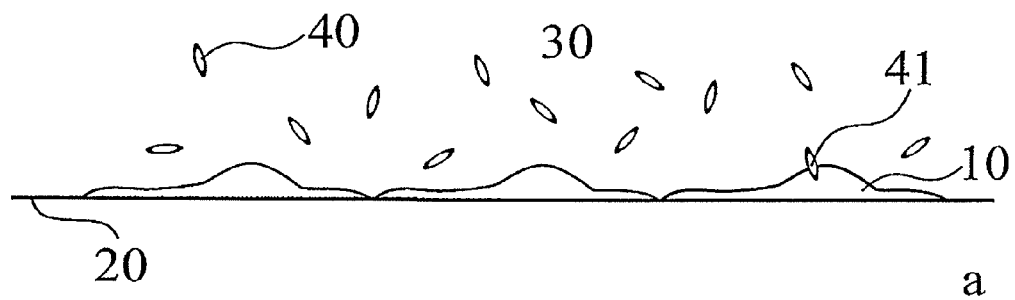
Figure 1:
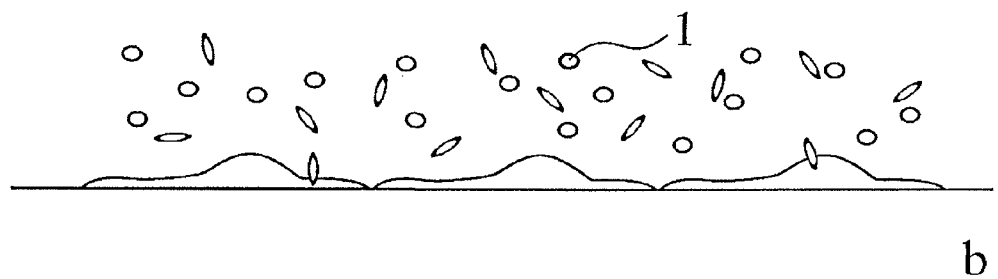
Figure 1:
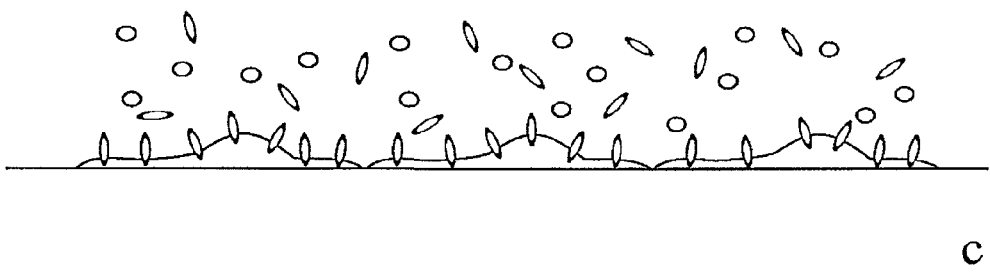

11 Claims, 12 Drawing Sheets a b c

METHOD AND APPARATUS FOR DETERMINING THE CELL ACTIVATION OF A TARGET CELL BY AN ACTIVATOR

The present invention claims priority to German Patent Application No. 10 2008 028 429.9 filed Jun. 17, 2008 and German Patent Application No. 10 2008 036 064.3-41 filed Aug. 4, 2008, the text of which is incorporated herein by reference.

The invention relates to a method and also a device for determining the cell activation of a target cell by an activator.

BACKGROUND OF THE INVENTION

Methods and devices of this kind are used, for example, in biomedical research, active ingredient research, biomaterial research or toxicology to analyze the activation of a target cell by an activator. Such studies are thus investigating whether activation is actually identifiable in a specific case and optionally also the aspect of more detailed characteristics of the activation, if activation can indeed be identified.

Many processes in the body of organisms are triggered by a cell, also referred to as a "target cell", coming into contact with a particle, with an extended solid or with another cell. The cell is activated by the contact. This means that contact between the cell and the particle, the solid or the other cell triggers cell-internal signals, then leading, for example, to a modified gene expression pattern of the cell. The cell is thereby converted into a new state and fulfils new functions.

One example of cell activation is the action of one or more adjuvants on the target cell. An adjuvant is often defined as an auxiliary substance which enhances the action, on the target cell, of substances having a specific action. In immunology an adjuvant is, for example, required in order to obtain an adequate immune response. Different adjuvants may also improve the immune response in a different manner. Where a vaccination is given, an adjuvant is, for example, also administered in order to ensure adequate protection by vaccination.

The exact mode of action of adjuvants is often still unknown, and their action is established empirically. In Europe at present only a very small number of adjuvants is approved for vaccination. For the discovery of an improved or new adjuvant, at present in immunology, for example, the immune response has to be analyzed at least in part. One of the ways of analyzing the immune response is to analyze the activation state of immune cells, for example of dendritic cells. This usually requires an appropriate antibody, which also has to be labeled with a fluorophore. An incubation period, which can easily last several hours, also has to be waited out. To achieve adequate statistics a sufficient number of cells is also required. In many cases an animal experiment will also be unavoidable if the action of the adjuvant is to be evaluated.

It is known that, for example, adjuvants cause activation or at least enhanced activation of immune cells. There are numerous further examples in immunology where, in very general terms, an activator activates a target cell which then, according to the activation, exhibits different behavior, at least in part, from before the activation. Thus, for example, T cells are activated only by dendritic cells and release cytokines, for example. B cells are activated by antigens and secrete corresponding antibodies. The generalized significance of particle-based cell activation is made clear by the mode of action of an active ingredient particle. An active ingredient particle becomes active only when, on contact, it activates a target cell.

A further example of particle-based cell activation is the action of a toxic particle. It is known that particles can develop a noxious action, for example when inhaled into the lung. The noxious action is produced only when the particle, on contact, activates a cell, for example a pulmonary epithelial cell.

One example of solid-based cell activation can be found in transplant technology. If, for example, a transplant material coming into contact with cells of a tissue leads to activation of the cells, this can lead to inflammation of the tissue, and the transplant is rejected. Generally speaking, in biomaterial research it must be ensured that the desirable cell activation occurs and undesirable cell activation is excluded.

Cell activation resulting from contact with other cells occurs, for example, in T cell selection and activation (Alberts et al., "Molekularbiologie der Zelle", VCH-Verlag, Weinheim, 1995), in the migration of neutrophils (Wagner et al., "Neutrophil Migration Mechanisms, with an Emphasis on the Pulmonary Vasculature", Pharmacological Reviews, Vol. 52, Issue 3, 349-374, 2000), in organogenesis generally or in processes connected with the formation of a cancerous ulcer or the formation of secondary cancers.

Probe microscopy (PM) is a measuring and analytical technique where, in a prominent design, a measuring probe is raster scanned over a sample of a measuring medium that is to be analyzed and where a topography of the sample is established by means of a distance-dependent interaction between the measuring probe and the sample. However, material constants or other sample information can also be obtained. Owing to the frequent use of a scanning process, the term scanning probe microscopy (SPM) is also often used instead of PM. There are different probe designs. The most prominent examples of PM are the atomic force microscope (AFM) and the scanning tunneling microscope (STM). Further examples of this technology are, in particular, the scanning near-field microscope (SNOM), the scanning photonice force microscope (SPhM) and the photonic force microscope. One further important analyzing method associated with probe microscopy is distance spectroscopy; here, for measurement purposes, the measuring probe is displaced usually only in a vertical direction relative to the sample analyzed. In this case both the instrument and the associated software can be reduced thereto.

To measure the distance-dependent interaction between the measuring probe and the sample, in distance spectroscopy the measuring probe is displaced relative to the surface of the sample, for example in a direction vertical to the sample surface, and the interaction between the measuring probe and the sample is measured. Alternatively the sample can also be moved. It is also possible to provide a relative movement between the measuring probe and the sample, where both the measuring probe and the sample are moved. In probe microscopy, this distance spectroscopy for measuring the interaction between the measuring probe and the sample is, for example, used to measure forces between molecules as one molecule binds to the measuring probe and a further molecule binds to the sample. The interaction between the two bound molecules can then be measured. It is, however, also possible to measure intramolecular forces, for example, by lowering the measuring probe onto the sample and binding is thus awaited. Thereafter the measuring probe can be removed from the sample again; during this process, forces thus acting on the measuring probe are recorded. Also possible are further measurements involving the measurement of an interaction which correlates with an associated distance between two or more locations.

In atomic force microscopy the measuring probe used is usually a component which is also referred to as a "cantilever". This can be used to measure forces by recording the deflection of the measuring probe. To minimize the interaction space and thus to improve lateral resolution, in many cases a measuring tip is attached to the free end of the cantilever. In the case of distance spectroscopy, however, instead of a tip being provided the cantilever is also, for example, specifically loaded with a cell; often the tip is then even dispensed with. Without loss of generality, reference is made in the explanations below to a cantilever. The statements apply accordingly to other forms of measuring probes in probe microscopy. Cantilevers are usually secured to a base, in particular to ensure reasonable handling.

It is known to use both untreated and also pre-treated cantilevers as measuring probes for distance spectroscopy. In the case of an untreated cantilever, binding of the sample during measurement is non-specific. For example, this involves pulling molecules from their surrounding medium by means of binding to the cantilever in order to measure the interaction of the molecules with the surrounding medium. However, this also makes it possible to characterize more precisely the molecules being pulled. Thus, for example, DNA molecules exhibit a specific spectroscopy curve on the basis of an internal conformational change.

A pre-treated cantilever enables an analysis to be made of, in particular, specific bonds. An analysis of this kind can be advantageous if the formation of undesirable bonds, which may possibly thereafter be virtually indistinguishable from each other, is to be prevented during measurement. Thus it is common practice to bind one or more molecules to the cantilever-type measuring probe, which then forms a receptor-ligand system with the bound molecule or molecules. It is also known to bind whole cells to a cantilever-type measuring probe and to bring this system into interaction with a sample, for example a biomaterial, or with other cells. In this case it may, for example, as already mentioned above, be beneficial to use a cantilever without a tip. Different forms of pre-treatment are known for measuring probes, in particular for cantilevers, for example that of making the measuring probe water-repellent.

Known possibilities for pre-treatment of the cantilever generally lead to coating of the measuring probe, at least sectionally. Thus a cell attached to the cantilever coats a section of the surface of the cantilever. In this case it is possible for the cantilever, in the course of the pretreatment, to be initially provided with a coating, in particular an adhesion-promoting coating, to which a substance to be measured is then applied. The material applied to the measuring probe, in particular the cantilever, in the course of the pretreatment is generally referred to hereafter as "probe substance", whether this be an individual material or a combination of a plurality of materials comprising, for example, an adhesion-promoting base and a substance arranged thereon and to be analyzed. A (base) coating applied in the course of the pretreatment and encompassed by the probe substance is also referred to as "probe coating".

SUMMARY OF THE INVENTION

The object of the invention is to provide a method and a device for determining the cell activation of a target cell by an activator, where the effort—in respect of time and/or materials—involved in analyzing the cell activation is reduced.

This object is achieved, according to the invention, by a method for determining the cell activation of a target cell by an activator as claimed in independent claim 1. Also provided is a device for determining the cell activation of a target cell by an activator as claimed in independent claim 13. Advantageous developments of the invention are the subject of dependent subclaims.

According to one aspect of the invention there is provided a method for determining the cell activation of a target cell by an activator, said method having the following steps: provision of a probe measuring device with a probe sample arrangement having a measuring probe and a sample holder; loading of the probe sample arrangement with a target cell and with an activator assigned to the target cell, the measuring probe being loaded with the activator, and the sample holder being loaded with the target cell, or vice versa; relative mutual displacement of the measuring probe and the sample holder until contact is made between the target cell and the activator by means of a displacement apparatus of the probe measuring device; recording of measurement values, indicating binding between the target cell and the activator, for the measuring probe with the probe measuring device during the relative displacement of the measuring probe and the sample holder; and determination of a dimension for the cell activation of the target cell from the measurement values recorded.

According to a further aspect of the invention there is provided a device for determining the cell activation of a target cell by an activator, having: a probe measuring device with a probe sample arrangement having a measuring probe and a sample holder; a displacement apparatus which is configured to displace the measuring probe and the sample holder, after loading of the measuring probe with an activator and of the sample holder with a target cell, or vice versa, relative to each other until contact is made between the target cell and the activator; a measurement control apparatus which is configured to record measurement values, indicating binding between the target cell and the activator, for the measuring probe during the relative displacement of the measuring probe and the sample holder; and a measurement evaluation apparatus which is configured to determine a dimension for the cell activation of the target cell from the measurement values recorded.

The invention enables activation of the target cell by the activator to be easily verified in a time-saving manner. In particular, the technologies proposed make it possible to identify whether or not the activator does actually lead to activation of the target cell, and this is analyzed on the basis of the interaction in the form of binding or non-binding between the target cell and the activator. To this extent binding forms an indicator of cell activation.

The target cell itself can be comprised of a group of cells. In one possible development a plurality of activators can also be arranged on the measuring probe. Conversely, a plurality of target cells can be arranged on the measuring probe. The measuring probe may, for example, be what is known as a "cantilever". The dimension for cell activation can be derived from one or more measuring variables recorded for the binding of the target cell.

Binding as understood here means all strong and weak bonds or all contacts between the target cell and the activator in general that give rise to a potential well and thus give rise to an attractive force between the binding partners. Strong bonds include, in particular, covalent bonds and ionic bonds. Weak bonds comprise, in particular, hydrogen bridge bonds, van der Waals bonds, and dipole-dipole and dipole-ion interactions. Further types of bond comprise, in particular, forces produced as a result of surface tension, for example two hydrophobic bodies brought into contact in an aqueous environment. Entropic forces are also bonds that are produced when configuration possibilities are limited.

The technologies proposed exhibit their advantages, in particular, where a plurality of activators and/or target cells is examined since, by comparison with prior art methods, the amount of time involved in determining cell activation is substantially reduced. The amount of material used is also distinctly reduced, in particular with regard to the need to provide extensive cell material or animal experiments.

In a preferred embodiment of the invention it was found that cells can be activated by contact with a particle, a solid or another cell. Cell activation takes place via a specific or non-specific receptor or as a result of the interaction of the lipids or of other components of the plasma membrane with a particle, a solid or another cell.

According to a preferred further development of the invention it is provided that an activation dimension for a cell-activated state of the target cell is also determined from the measurement values recorded.

In a purposeful embodiment of the invention, it can be provided that the measurement values are recorded as force measurement values. A preferred embodiment of force measurement is the recording of a force-distance curve. This makes it possible, in particular, to establish the adhesion between the activator and the target cell.

According to an advantageous embodiment of the invention it is provided that, when the measurement values are recorded, a time curve of a measuring variable indicating binding or non-binding between the target cell and the activator is recorded. Activation of the target cell by the activator can be inferred, in particular, if the time curve indicates an increase in binding between the target cell and the activator.

According to a development of the invention it can be provided that during the relative mutual displacement of the measuring probe and the sample holder, the target cell and the activator are preferably repeatedly brought into contact and separated from each other.

In an advantageous embodiment of the invention it can be provided that the probe measuring device provided is a probe microscope and the measurement values are recorded as probe microscopy measurement values.

According to a further development of the invention it can be provided that probe microscope provided is a scanning probe microscope and the probe microscopy measurement values are recorded as scanning probe microscopy measurement values.

According to a preferred further development of the invention it is provided that the probe microscope provided is an atomic force microscope and the probe microscopy measurement values are recorded as atomic force microscopy measurement values.

In a purposeful embodiment of the invention it can be provided that the activator is bound to the measuring probe or the sample holder by means of an activator adhesion promoter. The use of the activator adhesion promoter enables possible interaction of the activator with the measuring probe or with the sample holder itself to be neutralized in order to avoid measurement distortions possibly caused thereby.

According to an advantageous embodiment of the invention it is provided that the target cell is bound to the measuring probe or the sample holder by means of a cell adhesion promoter. The cell adhesion promoter is preferably selected such that it does not itself cause activation of the target cell.

According to a development of the invention it is provided that a plurality of measurement series is preferably recorded for the measurement values. The plurality of measurement series can be recorded at time intervals. It is thus possible, for example, to provide equal time intervals between different measurement series. However, a random distribution of the time intervals between the measurement series can also be used. The recording of a plurality of measurement series also makes it possible, in particular, to record variations over time in the bond between the target cell and the activator in the form of binding or non-binding.

In an advantageous embodiment of the invention it can be provided that the activator used is a material selected from the following group of materials: active ingredient particle, implant material, aerosol, adjuvant and activator cell.

In the case of an adjuvant it is possible to carry out a method in which an activator action can be very quickly evaluated, such that a pre-selection of adjuvants can be made from a large group of candidates. In the case of an implant, it is possible to verify whether or not a material causes an inflammatory reaction. In the case of aerosols, the method can be used to verify whether the aerosols have a toxic effect in the lung or can enter the bloodstream through the lung and have a toxic effect in the body or whether they cause an inflammatory reaction in the lung or in the remainder of the body. In the case of an active ingredient particle, it is possible to analyze whether the particle does actually interact with target cells and can thus potentially be effective. The method also makes it possible to tackle issues in basic research in immunology, in cancer research, or the like, where activation of a target cell as a result of interaction with a particle, a solid or another target cell is directly analyzed.

Measurement of the bond between an activator and a cell that is to be activated, i.e. the target cell, enables a selection to be made in respect of the effect achieved by the activator. Furthermore, evidence of the activation state of the target cell can also be obtained from the bond. A desirable activation can also be brought about by selectively inducing binding with a target cell.

The appropriate target cell should be established for the process to be analyzed as the case arises and is selected from the group of cells of interest for an application to be analyzed. It may be advantageous to analyze a large number of different cell types in different states. If the target cell or a group of target cells is found, a plurality of different activators can be tested thereon.

One advantage over the prior art is therefore the fact that only the activator and the target cell are now required. The effect of activation by the activator does not therefore have to be tested indirectly by means of the action, for example the expression of new proteins. The effect can be inferred directly from the bond itself. In other cases the invention makes it possible to select, from a large number of cell types and/or activators, those which categorically bind with each other and result in activation. Further studies on the exact nature of the interaction in the form of binding are thereby restricted to these interaction partners.

One further advantage is that a single measurement is involved, that is to say, in the simplest case only an activator and a target cell are required. For this purpose the activator can be bound to the measuring probe and the target cell to the sample support. A converse arrangement can also be provided, however. Which version is selected will, in the individual case, be made dependent on which combination is easier to prepare.

According to one possible embodiment of the invention, the target cell is an immune cell, in particular a dendritic cell.

According to one possible further development of the invention, activation is prevented during preparation of the target cell, for example while it is being secured to the cantilever or to the sample holder. One possible method is, for example, to use CellTac to immobilize the cell (for details of CellTac, cf. Waite et al., "Polyphenolic Substance of *Mytilus*

*edulis*: Novel Adhesive Containing L-Dopa and Hydroxyproline", Science 212 (1981): 1038-1040). In the case of the PFM (photonic force microscope) it is also possible optionally to dispense with immobilization of the target cell and/or of the activator.

According to a further development, the corresponding substance and/or the adjuvant are prepared in such a way that binding is possible. If, for example, small molecules are to be tested as adjuvants, it may be better to secure these molecules to, for example, a small particle and then to attach this particle to the cantilever. This then guarantees that only the adjuvant is involved in the interaction and not, for example, the silicon of a cantilever. In addition to this solution, the adjuvant can also be joined to the cantilever by means of an elongated molecule. This method has the advantage that binding can develop more flexibly and therefore more in line with the natural process. For example, the adjuvant can complete a rotation so as to complete an interaction in the correct configuration.

It is also possible to allow a single interaction to take place only in a limited manner and to measure that interaction. Repeated measurement at suitable time intervals enables a trend in the variation of the interaction to be registered and thereby evidence of effectiveness to be obtained. Suitable time intervals should be selected such that an interaction, for example force, is within the measuring capabilities of the measuring instrument. The time intervals selected can be equidistant. It is, however, also possible for stochastic time intervals to be selected in order thus to simulate, for example, the natural process that may take place in this manner.

DESCRIPTION OF PREFERRED EXEMPLARY EMBODIMENTS OF THE INVENTION

Figure 3:
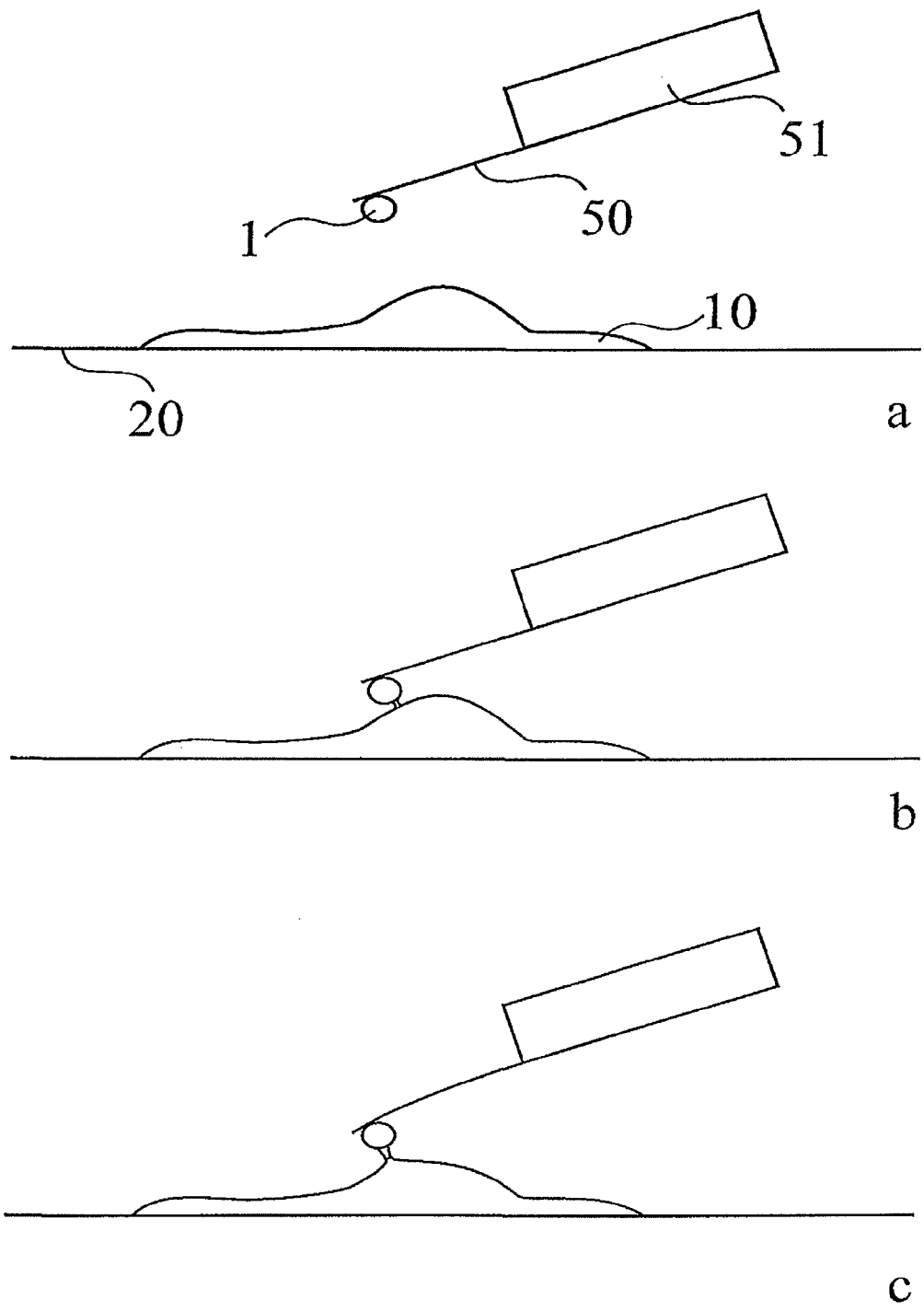
Figure 4:
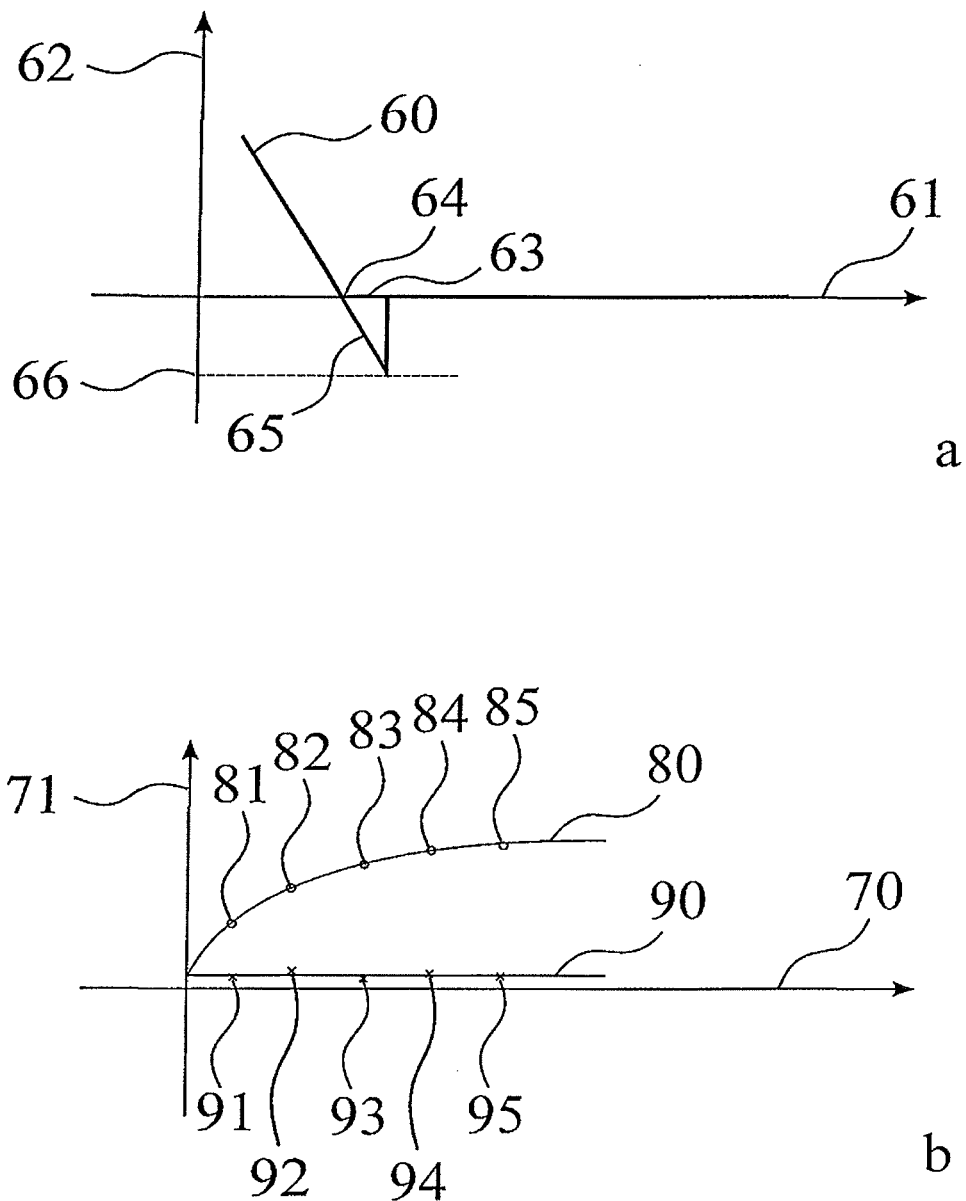
Figure 5:
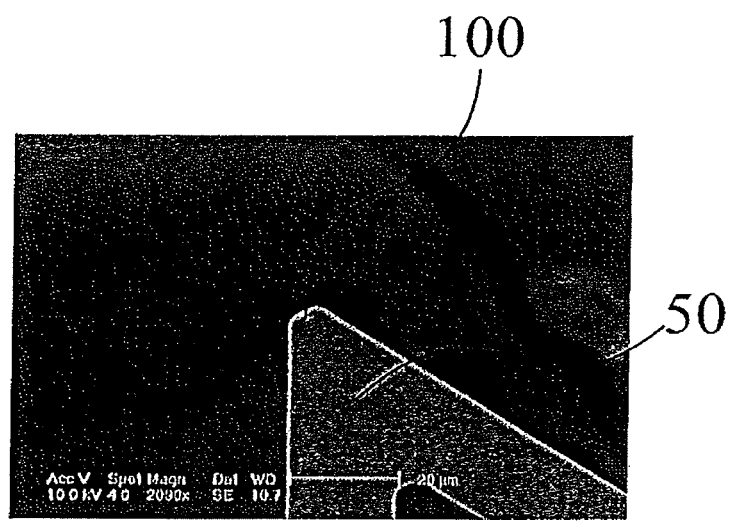
Figure 6:
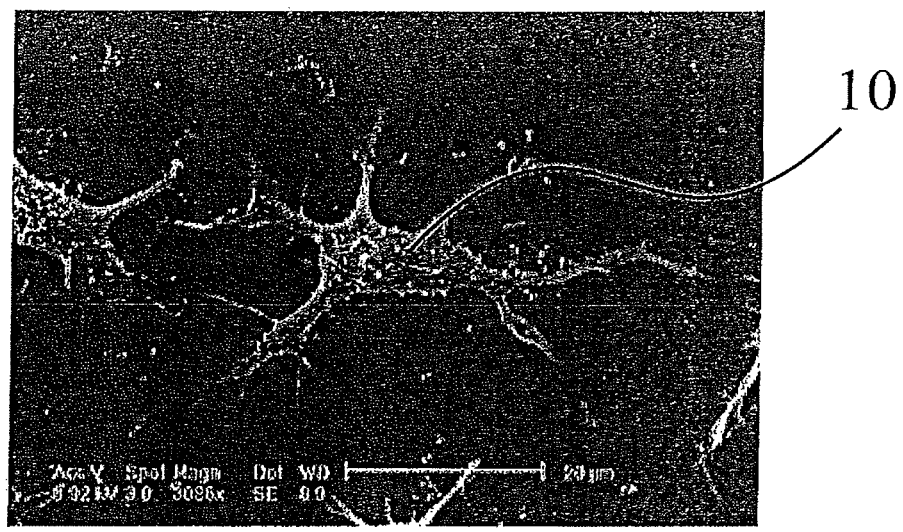
Figure 7:
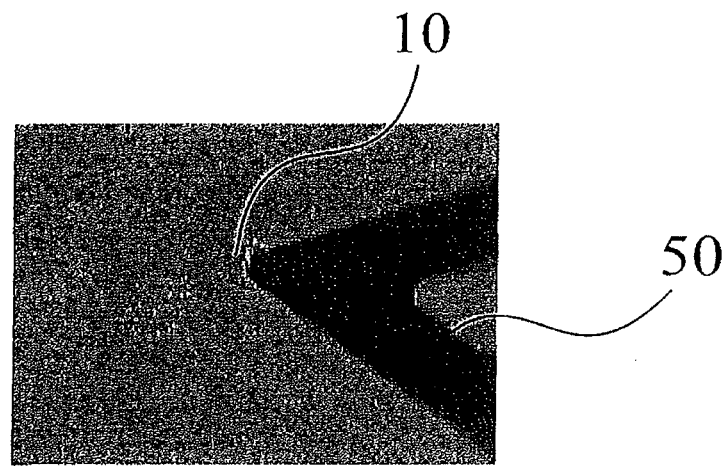
Figure 8:
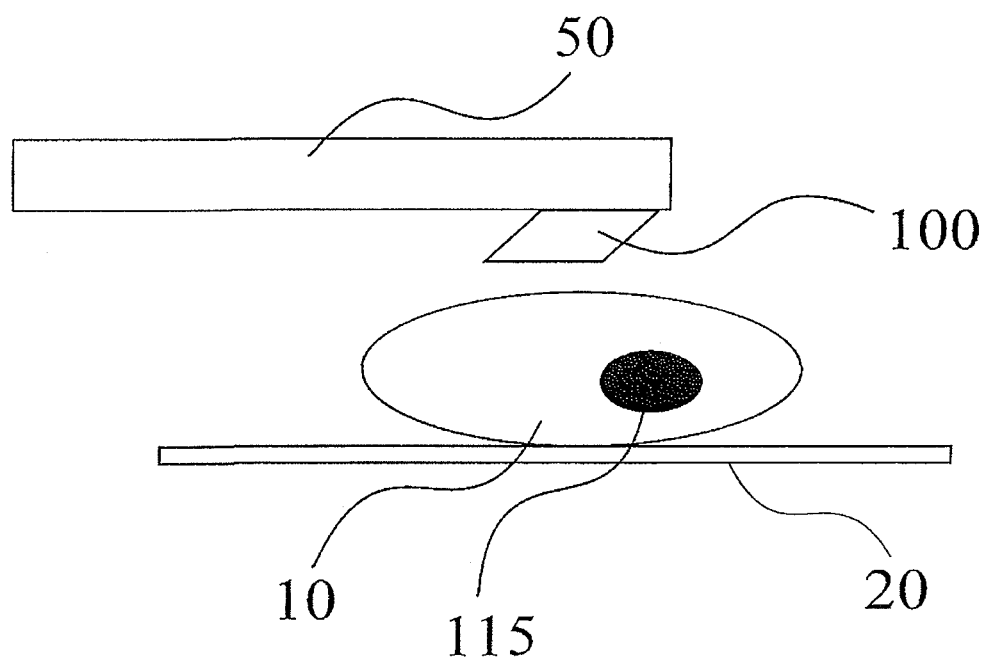
Figure 9:
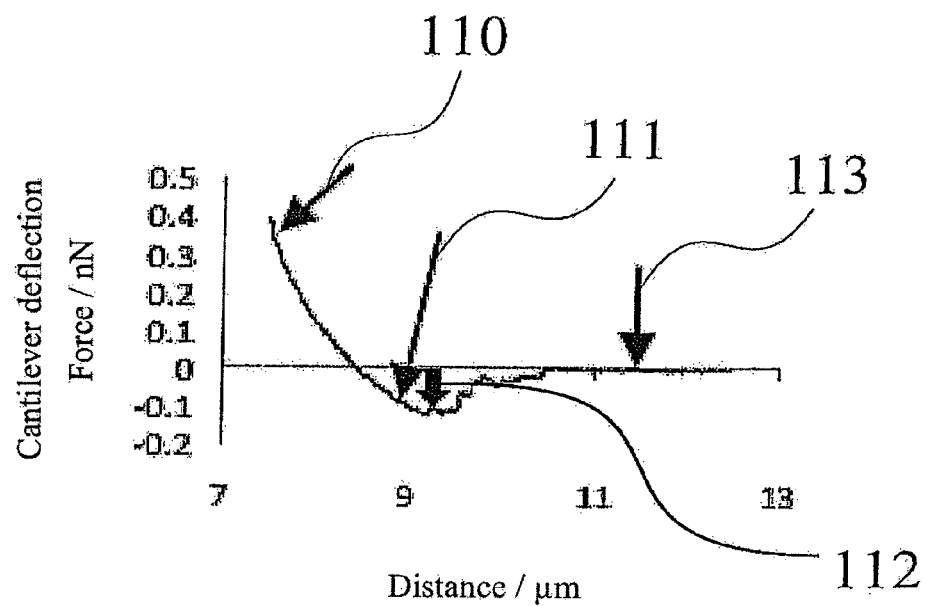
Figure 10:
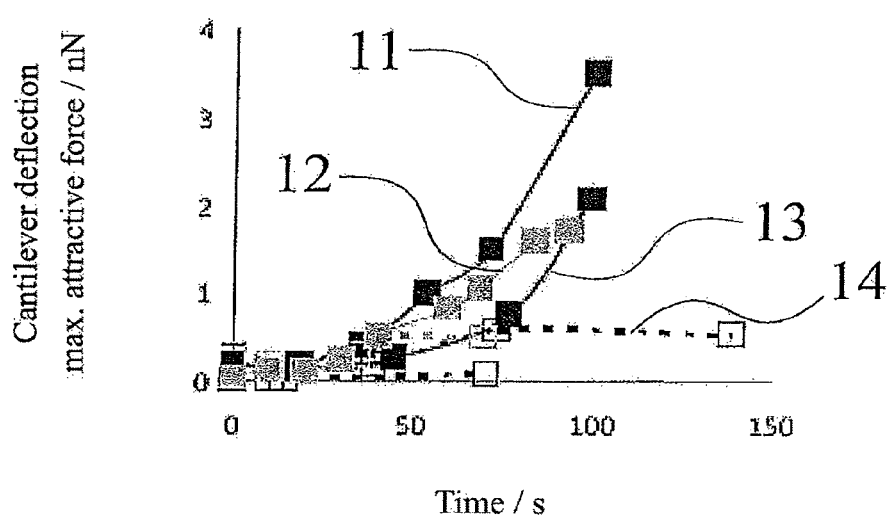
Figure 11:
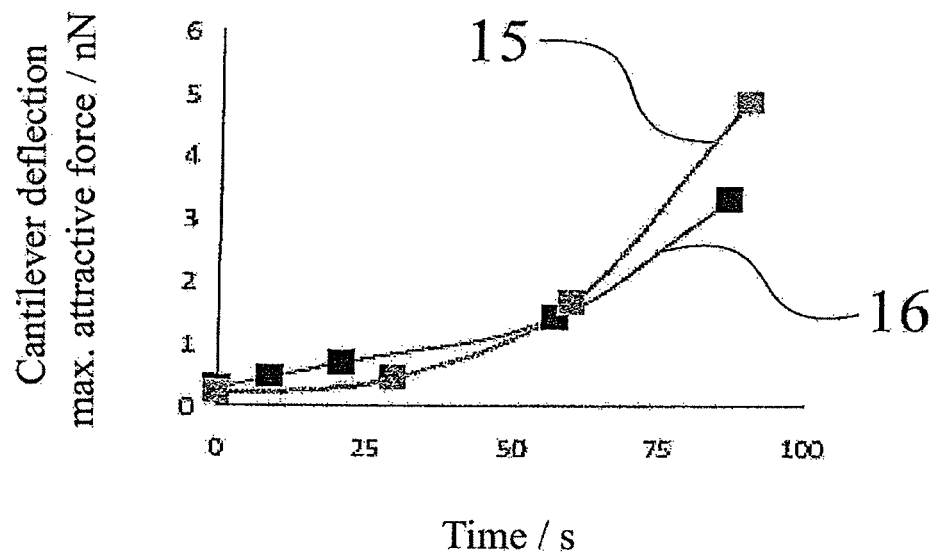
Figure 12:
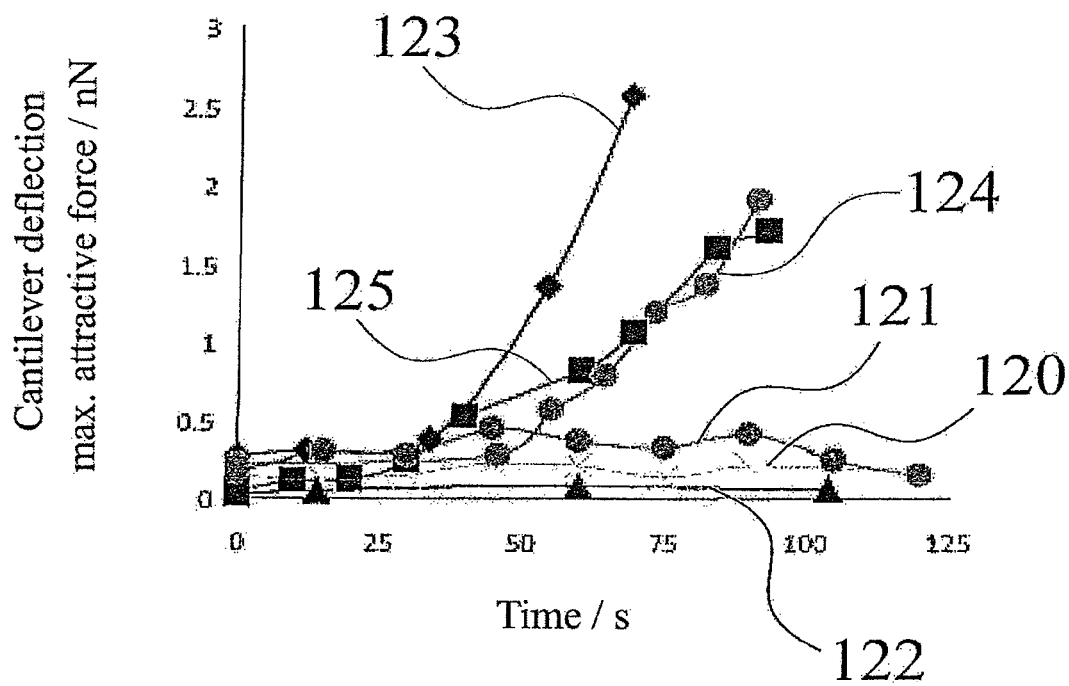
Figure 13:
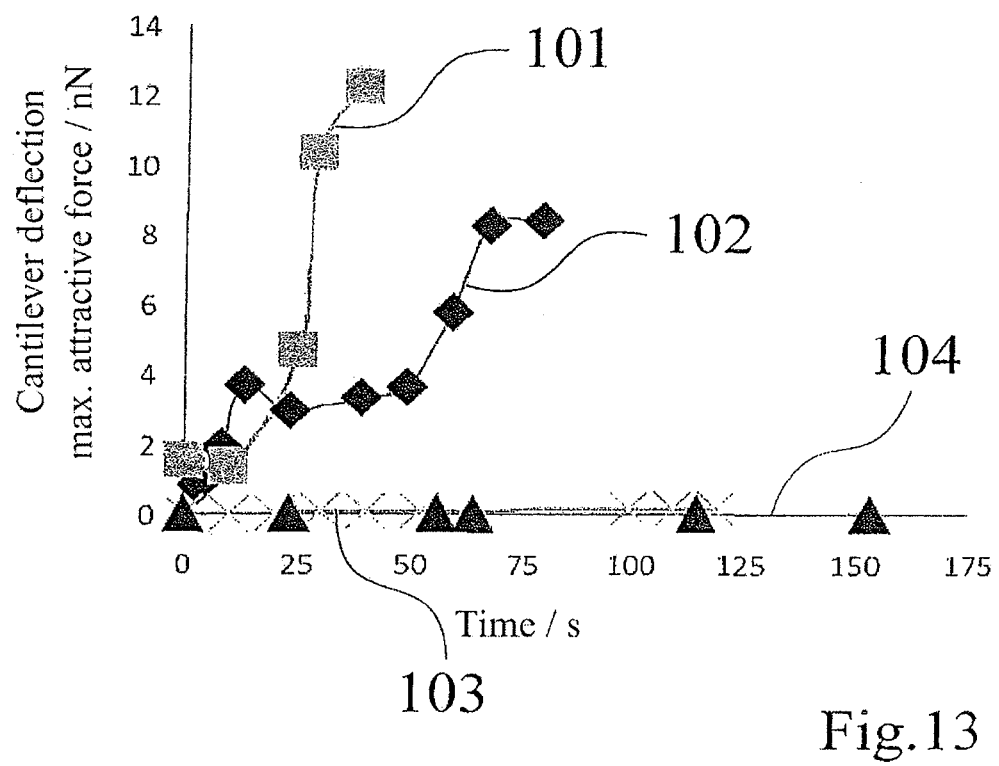
Figure 14:
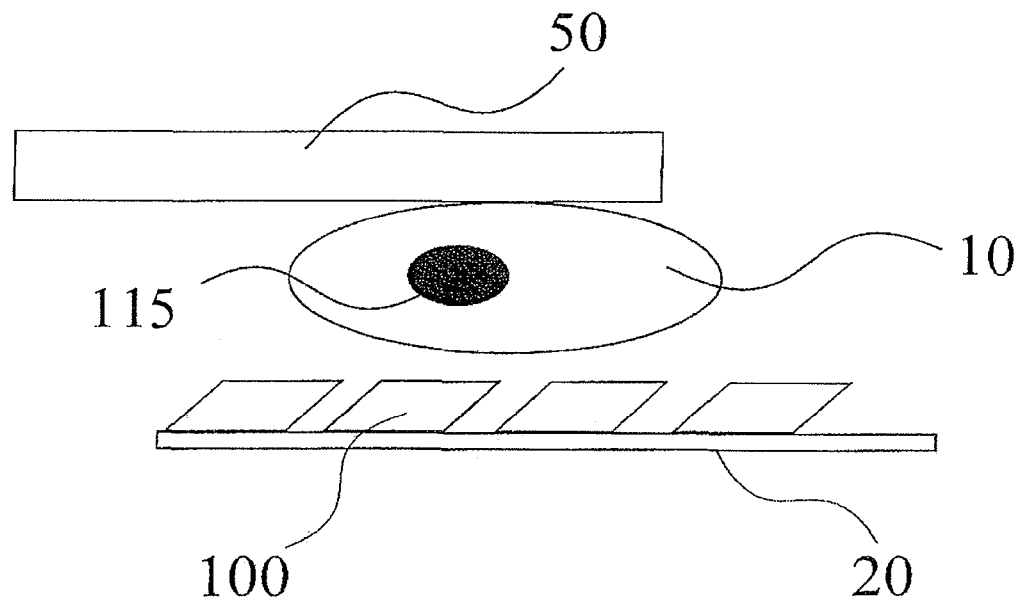
Figure 15:
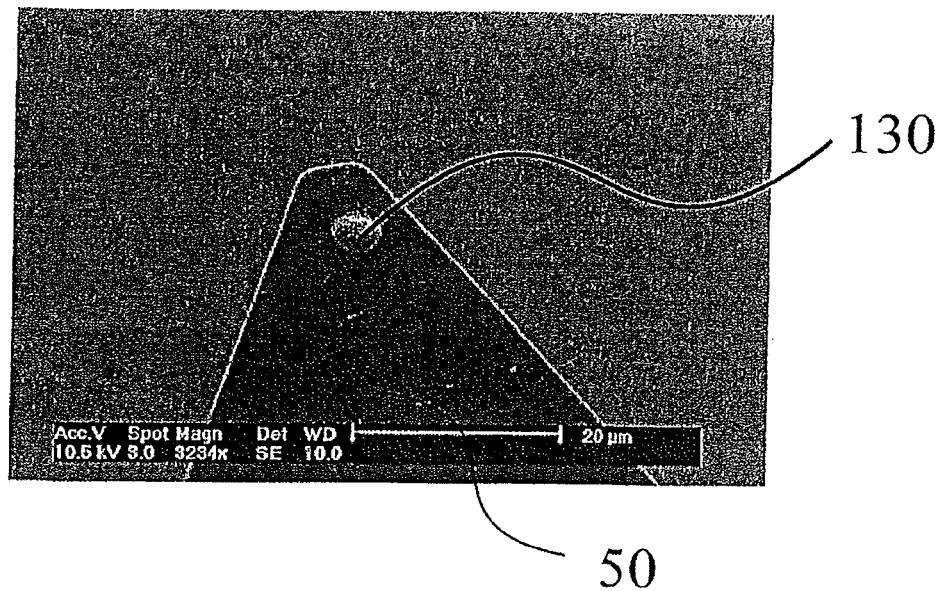
Figure 16:
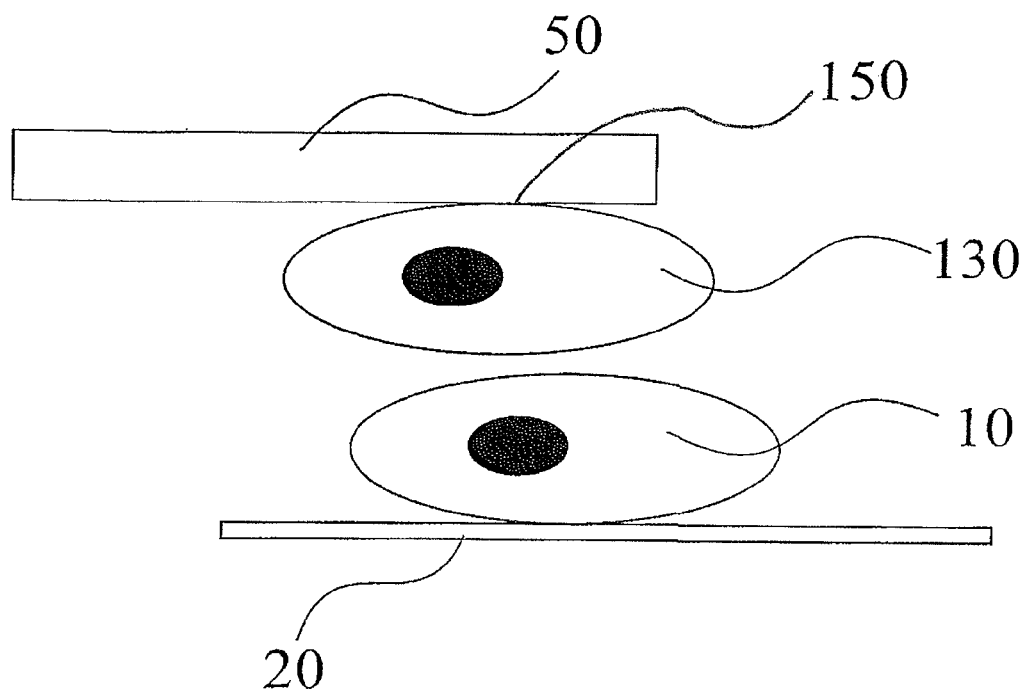
Figure 17:
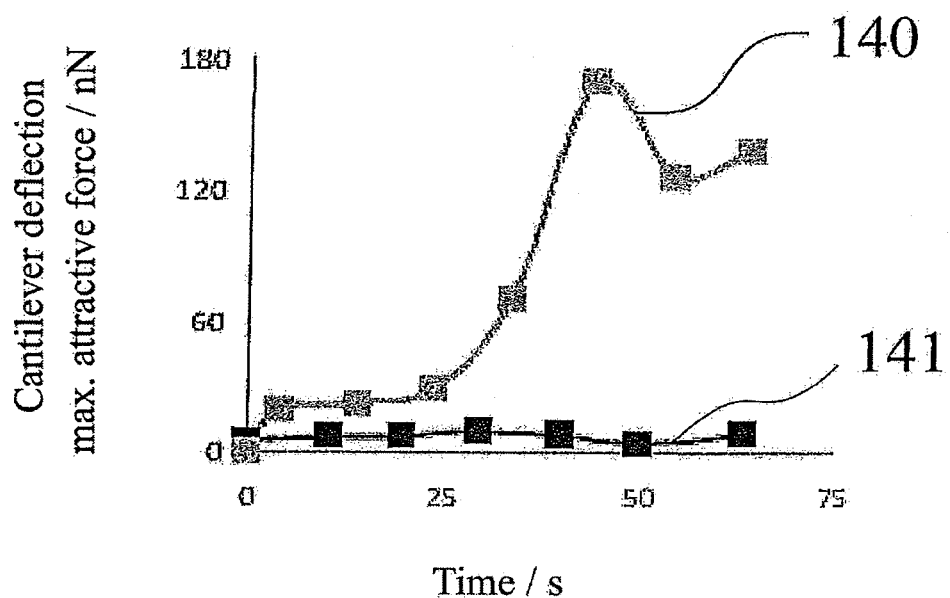
Figure 18:
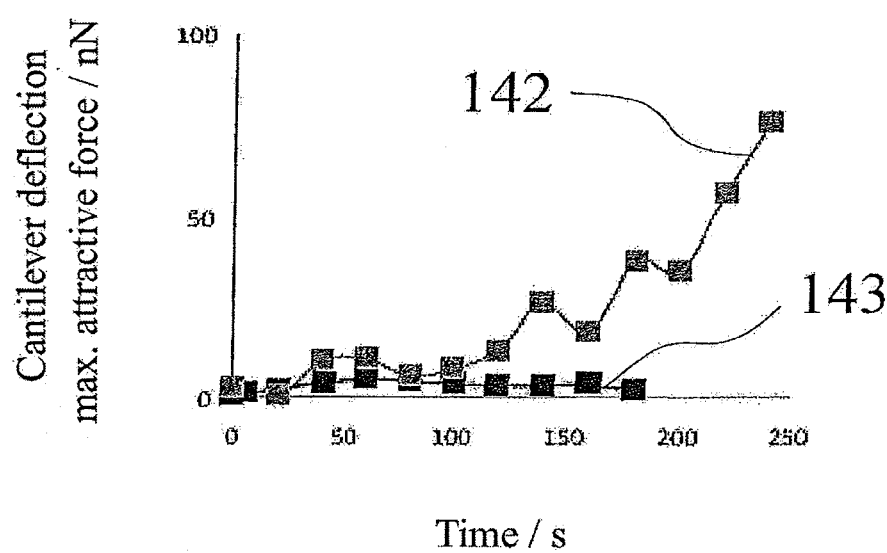
Figure 19:
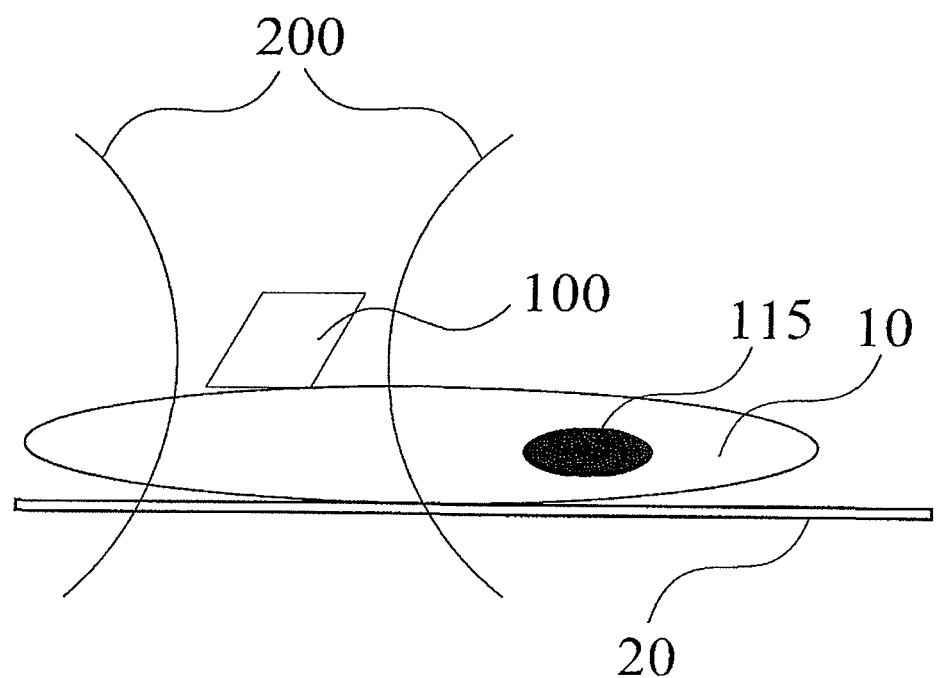

The invention is explained in more detail hereafter by means of preferred exemplary embodiments, with reference to figures in a drawing in which:

FIG. 1 shows a schematic representation a known method for determining cell activation using the example of immunology, FIGS. 2*a* and 2*b* show a schematic representation of an arrangement with an adjuvant and a target cell, FIG. 3*a* to 3*c* show a schematic representation of an arrangement with a target cell and an activator on a measuring probe, FIGS. 4*a* and 4*b* show graphical representations of measurement curves for the determination of cell activation between a target cell and an activator, FIG. 5 shows a cantilever on which a monosodium urate crystal is arranged as activator, FIG. 6 shows a photograph of a dendritic cell (DC), FIG. 7 shows the cantilever with the monosodium urate crystal of FIG. 5 over the dendritic cell of FIG. 6, FIG. 8 shows a schematic representation with a measuring arrangement, FIG. 9 shows a graphical representation of an exemplary characteristic of a measured force-distance curve, FIG. 10 shows a graphical representation of the time curve of values from force-distance curves for dendritic cells (DC2.4, THP-1, TMDC), FIG. 11 shows a graphical representation of the time curve of values from force-distance curves for a dendritic cell before and after the removal of surface proteins, FIG. 12 shows a graphical representation of the time curve of values from force-distance curves for different kinase inhibitors, FIG. 13 shows a graphical representation of the time curve of values from force-distance curves for different particles whose effectiveness as activators is to be tested, FIG. 14 shows a schematic representation of a measuring arrangement for measuring the measurement values shown in FIG. 13, FIG. 15 shows an arrangement having a cantilever, to which a T cell is bound, FIG. 16 shows a schematic representation of a measuring arrangement for the cantilever in FIG. 14, FIG. 17 shows a graphical representation of the time curve of values from force-distance curves for a T cell line which comes into contact with a dendritic cell, FIG. 18 shows a graphical representation of the time curve of values from force-distance curves for a further T cell line in contact with a dendritic cell, and FIG. 19 shows a schematic representation with a measuring arrangement, wherein a measuring probe is formed by means of a laser focus.

FIG. 1*a* to 1*c* show a schematic representation of a known method for determining cell activation using the example of immunology.

FIG. 1*a* shows a cell culture with immune cells 10 on a sample support 20. The immune cell here may be, for example, a dendritic cell. In the medium surrounding the cells, which generally consists of an aqueous buffer 30, there are disposed antigens 40 which are sporadically taken up by a cell and presented on the surface thereof 41. This presentation constitutes possible "activation" of the cell. It is also possible for no antigen to be presented and thus for no activation to have occurred.

In FIG. 1*b*, the adjuvant 1 to be analyzed is now additionally added to the surrounding medium 30. After an incubation period, a distinct increase in the presentation of antigens 41 on the surface of the cells can be seen in FIG. 1*c*. Activation of the cells is thus distinctly increased. For the example shown it is now a matter of demonstrating the differences in antigen presentation between FIGS. 1*a* and 1*c*. For this there are numerous analyzing methods such as, for example, the fluorescence methods FACS (fluorescence-activated cell sorting) or the like.

In addition to the possibility indicated, there are many further activation possibilities and these can, for example, consist in the release of messengers. These differences must also be demonstrated, for example by means of biochemical methods, or by means of a further subsequent activation of a further cell. In all cases, only ever the action is demonstrated.

FIGS. 2*a* and 2*b* show a very simple arrangement for evaluating an adjuvant using the example of immunology, with FIG. 2*a* showing first only an adjuvant 1, i.e. the activator, and a dendritic cell 10, i.e. the target cell, on a substrate 20. If binding 2 now takes place between the adjuvant 1 and the cell 10, as shown in FIG. 2*b*, this bond can in principle be measured and is used as a dimension for the action of the adjuvant on enhanced activation of the cell. Unlike in known methods, actual activation of the cell is therefore more of an indirect subject of analysis here, which substantially simplifies the analysis.

Figure 2:
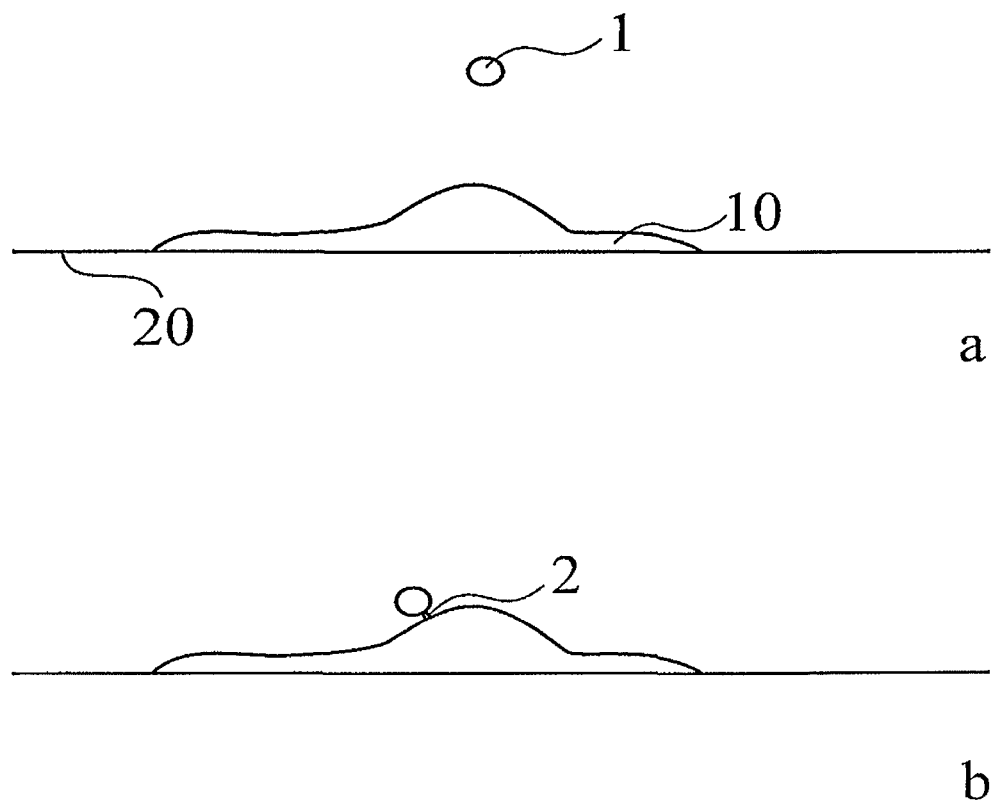

FIG. 3*a* to 3*c* show a schematic representation of an arrangement with a target cell and an activator on a measuring probe to explain a measurement method for the measurement of the bond explained in FIG. 2.

An adjuvant 1 is bound to a cantilever 50. The cantilever 50 is designed without a tip and is, in the usual manner, secured to a base 51. This base 51 is used to provide an attachment to the atomic force microscope, the components of which are known and, for simplification, are not shown here. The deflection of the cantilever 50 now makes it possible to measure, for example, a force. As in FIGS. 2a and 2b, a cell 10 is again immobilized on a substrate 20. In the present example, approximation of the adjuvant and the cell is now brought about by means of a relative vertical movement between the substrate and the base 51 until a bond 2 can form. If an attempt is now made to distance the adjuvant from the cell by a fresh movement between the substrate and the base, as shown in FIG. 3c, the cantilever 50 is deflected and thus a force is measured. This measurement is a possible characterization of the bond discussed in conjunction with FIGS. 2a and 2b and provides evidence of the activation effectiveness of the adjuvant 1.

In this way, for example, it is possible to identify an optimal adjuvant from a large selection of possible adjuvants. Further parameters such as, for example, pH value or the initial state of the target cell, can enable an appropriate adjuvant to be selected for a specific situation.

FIGS. 4a and 4b show graphical representations of measurement curves for the determination of cell activation between a target cell and an activator to explain an embodiment of a measurement method having the advantage of representing a development over time.

By way of introduction, a typical force-distance curve 60 is once again delineated in FIG. 4a. The x-axis 61 shows the relative distance between the substrate 20 and the base 51 as defined in FIG. 3; the y-axis 62 shows the deflection of the cantilever, which can inter alia also be interpreted as force. In a simplified case it can initially be assumed that the deflection of the cantilever for the approximation and distancing of the substrate and the base differs only in proximity to the contact. The approximation curve then extends in the section 63; the cantilever is deflected not here but only at the point 64 when the adjuvant comes into contact with the cell. When distancing occurs, the characteristic 65 is then often observed if a bond has formed between the adjuvant and the cell.

The force under which detachment and thus separation of the adjuvant and the cell occurs is generally referred to as the adhesive force 66. Thereafter there is no action of force, and the cantilever is no longer deflected. The adhesive force 66 can now be used as a dimension for an evaluation of the adjuvant.

To obtain particularly reliable evidence, the measurement sequence shown in FIG. 4b is provided in the present exemplary embodiment. For this the x-axis 70 is plotted, for example, as the time axis and the y-axis 71 as the adhesive force. The round points 81, . . . , 85 now indicate a characteristic 80 of five measurements of the adhesive force, where the adhesive force increases successively. The adjuvant forms a bond and can therefore be considered effective. The crosses 91, . . . , 95 indicate an adjuvant where an adhesive force is also present but where the sequence 90 over time does not show any development and can therefore be classified as non-specific; in this case the adjuvant is classed as ineffective or at least as more ineffective than the one considered above and represented in characteristic 80.

The individual points can also represent an averaging of a plurality of force-distance curves, since otherwise the non-specific scatter might prevent the development from being seen. The reason for this measurement method is that, in a known method where, for example, the residence time is extended, the forces quickly become too great, so they can no longer be measured. A single measurement would not itself be useful, owing to possible and even considerable non-specific forces. The proposed measurement method could also have an advantage in that the sequence is closer to the natural process. The present improved measurement method can, of course, also be modified by varying different parameters such as, for example, residence time, maximum contact force, pH value, temperature or the like, such that it is possible to estimate their influence.

FIG. 5 shows a cantilever 50 on which a monosodium urate crystal (MSU crystal) 100 is secured as activator.

FIG. 6 shows a dendritic cell (DC) 10 as target cell. Dendritic cells belong to a group of immune cells which activate the immune system in the presence of pathogens or even particles. The MSU crystal, being such a particle, causes very strong activation. Research studies are trying to discover which mechanism underlies this process.

FIG. 7 shows a cantilever 50, with an MSU crystal which is not, however, visible in this photograph, above a dendritic cell 10. In FIG. 8 the set-up is sketched again schematically, in this case showing not only the cantilever 50 and the dendritic cell 10 having the nucleus 115 but also the MSU crystal 100 and the sample support, a glass plate 20.

FIG. 9 shows a measured force curve as produced following mutual displacement of the cantilever and the sample holder. The approximation itself is not shown here, only the pulling away from each other. What ensues is a repulsive regime, arrow 110, which occurs when the cantilever presses into the cell. If the distance between the cantilever and the sample holder is now increased, the point is reached where the cantilever is no longer deflected, that is to say the force is 0 nN. Owing to attractive forces, the cause of which is a bond in the sense understood here, the cantilever is now deflected again, however, and the attractive regime ensues (arrow 111). The maximum force occurring here (arrow 112) is now evaluated. Alternatively, for example, the calculated area below the curve or a similar dimension can also be used. If the cantilever and the cell are distanced far enough from each other, then the cantilever is no longer deflected, and no further interaction takes place between the two (arrow 113).

If the method now used is that presented above with reference to FIG. 4a to 4c, where a force-distance curve was captured every second for the present system, then, as shown in FIG. 10, ever increasing binding forces will be measured, with different lines of dendritic cells (DC2.4 (11), THP-1 (12) and BMDC (13)) having been tested. This indicates activation of the dendritic cell. For a cantilever without an MSU crystal there is no appreciable variation in the adhesive force (14) for two measurement series.

FIG. 11 shows that the force-distance curve characteristic does not substantially alter if the experiment is carried out with a dendritic cell from which all the surface proteins are removed, this being carried out here by carrying out a treatment with pronase. The characteristic 15 shows a measurement with an untreated cell; the characteristic 16 shows a measurement with a cell treated with pronase.

Now if all the cholesterol is removed from the cells, the characteristic will alter such that no further variation in the adhesive force occurs over time (not shown). It is therefore concluded that an alteration in the arrangement of cholesterol on the membrane triggers a signal cascade for activation. Involved in this is, for example, SYK (spleen tyrosine kinase), a human protein and gene. SYK, together with Zap-70, is a member of the Syk family of tyrosine kinases. These non-receptor cytoplasmic tyrosine kinases share a characteristic double SH2 domain which is separated by a linker domain. Although SYK and Zap-70 are expressed mainly in hematopoietic tissue, they are also expressed in a plurality of other tissues. In both B lymphocytes and T lymphocytes, SYK and Zap-70 relay signals from the B or T cell receptors. SYK fulfils the same function in the case of signal transmission from a plurality of cell surface receptors, including CD74, FC receptor and integrins.

Now for different inhibitors very different characteristics again ensue for the maximum binding force over time, and these are shown in FIG. 12. For piceatannol (120), an SYK inhibitor, and wortmannin (121) and LY 294002 (122), both inhibitors of PI3K kinase, the characteristics produced suggest that no activation takes place. For an external blocker such as FcR g (123) or a control inhibitor (124) and also for an untreated sample (125), again an increase in the maximum binding force over time ensues, suggesting activation.

Other particles were also tested, thus for example latex, BCP and allopurinol. The results are shown in FIG. 13. For comparison the characteristic of an MSU test 101 is shown. Latex, which is likewise known to trigger activation, again shows the increase in binding forces 102; BCP 103 and allopurinol 104 (triangles), which do not activate, show no increase. The method is thus tested on a plurality of structures. Together with the above-described measurements and findings, the use of the force measurement method, in particular also the time curve thereof, is proposed as a general indicator of cell activation.

The experimental set-up is once again sketched schematically in FIG. 14. In this case the dendritic cell 10 having the nucleus 115 is secured to a cantilever 50. The activator, here the MSU crystal 100, is in this case arranged on a glass support 20, for example as a crystal surface consisting of a plurality of crystals.

FIG. 15 shows an arrangement having a cantilever 50, to which is bound a T cell 130 from the OT-2 cell line. FIG. 16 is a schematic representation of the measuring arrangement with the cantilever 50, with the T cell 130 bound thereto by means of a cell adhesion promoter 150, and with a dendritic cell 10 which is bound to a surface 20. If the cell is secured to the cantilever using a common method, an unacceptable activation already occurs beforehand. For this reason a non-activating cell adhesion promoter is used here, for example Cell-Tak.

Now if the T cell contains peptides in the form of antigen receptors, such that activation of the T cell should be triggered, an increase in the binding force 140 again ensues, as shown in FIG. 17. In the control experiment without peptides, no significant increase in the binding force ensues 141. In this example with the T cell line OT-1, the dendritic cell is therefore not, as previously, activated; instead, the dendritic cell itself is the activator here and the T cell is the target cell. For validation purposes the experiment was repeated with a T cell from another cell line, OT-2, and similar results are shown in FIG. 18, that is to say an increase in the binding force over time where antigen receptors are present 142, and no increase in the binding force where no receptors are present 143.

Where a PFM (photonic force microscope) is used, it is optionally also possible to dispense with immobilization of the target cell and/or of the activator. In the example in FIG. 19, the experiment of FIG. 8 has been modified here such that the probe is no longer a cantilever but a laser focus, which is sketched as a Gaussian beam path 200. A particle 100, for example an MSU crystal or another suitable particle, is held in the focus. By detecting the light scattered at the particle 100 it is, at the same time, possible to measure the forces on the particle, which can then possibly even be smaller than in the case of the SFM.

The features of the invention disclosed in the above description, in the claims and in the drawing may, both individually and in any combination, be significant for the performance of the invention in its different embodiments.

The invention claimed is:

1. A method for determining the dimension for cell activation of a target cell, said method comprising the steps of:
   providing a probe measuring device with a probe sample arrangement having a measuring probe and a sample holder,
   loading the probe sample arrangement with a target cell and loading the measuring device with an activator assigned to the target cell, and loading the sample holder with the target cell, or vice versa, displacing the measuring probe and the sample holder so that relative mutual displacement of the measuring probe and the sample holder happens until contact is made between the target cell and the activator by a displacement apparatus of the probe measuring device, and when contact between the target cell and the activator is made internal signals are triggered in the target cell by the activator, converting the target cell from a ground state into an excited state, in which the target cell fulfills new functions,
   recording measurement values, indicating binding between the target cell and the activator, for the measuring probe with the probe measuring device during the relative displacement of the measuring probe and the sample holder, wherein the relative displacement of the measuring probe and the sample holder includes moving the measuring probe away from the sample holder after contact between the target cell and the activator is made, and
   determining a dimension for the cell activation of the target cell from the measurement values recorded.

2. The method according to claim 1, wherein said step of recording the measurement values includes recording the measurement values as force measurement values.

3. The method according to claim 1, wherein said step of recording includes recording a time curve of a measuring variable indicating binding or non-binding between the target cell and the activator when the measurement values are recorded.

4. The method according to claim 1, wherein said step of displacing includes repeatedly contacting and separating the target cell and the activator during the relative mutual displacement of the measuring probe and the sample holder.

5. The method according to claim 1, wherein said step of providing the probe measuring device includes providing a probe microscope and said step of recording the measurement values includes recording the measurement values as probe microscopy measurement values.

6. The method according to claim 5, wherein said step of providing the probe microscope includes providing a scanning probe microscope and said step of recording measurement values includes recording the measurement values as scanning probe microscopy measurement values.

7. The method according to claim 1, wherein said step of providing the probe microscope includes providing an atomic force microscope and said step of recording measurement values includes recording the measurement values as atomic force microscopy measurement values.

8. The method according to claim 1, wherein said step of loading the activator includes binding the activator to the measuring probe or the sample holder of an adhesion promoter.

9. The method according to claim 1, wherein said step of loading the target cell includes binding the target cell to the measuring probe or the sample holder by a cell adhesion promoter.

10. The method according to claim 1, wherein said step of recording measurement values includes recording a plurality of measurement series for the measurement values.

11. The method according to claim 1, wherein said step of providing the activator includes selecting the activator from the following group of materials: active ingredient particle, implant material, aerosol, adjuvant and activator cell.

* * * * *